(12) United States Patent
Hirao et al.

(10) Patent No.: US 6,706,907 B1
(45) Date of Patent: Mar. 16, 2004

(54) METHOD OF PURIFYING ORGANIC PHOSPHORIC ESTER

(75) Inventors: Kiyoharu Hirao, Sennan (JP); Masasuke Oda, Ashiya (JP)

(73) Assignee: Daihachi Chemical Industry Co. Ltd., Osaka (JP)

( * ) Notice: Subject to any disclaimer, the term of this patent is extended or adjusted under 35 U.S.C. 154(b) by 0 days.

(21) Appl. No.: 10/030,124

(22) PCT Filed: Jun. 19, 2000

(86) PCT No.: PCT/JP00/04003
§ 371 (c)(1),
(2), (4) Date: Jan. 24, 2002

(87) PCT Pub. No.: WO01/12638
PCT Pub. Date: Feb. 22, 2001

(30) Foreign Application Priority Data

Aug. 18, 1999 (JP) ............................................ 11/231704

(51) Int. Cl.⁷ .................................................. C07F 9/02
(52) U.S. Cl. ...................................... 558/146; 558/147
(58) Field of Search ................................ 558/146, 147

(56) References Cited

U.S. PATENT DOCUMENTS

| | | |
|---|---|---|
| 4,049,617 A | 9/1977 | Albright |
| 5,206,404 A | 4/1993 | Gunkel et al. |
| 5,401,788 A | 3/1995 | Tokuyasu et al. |
| 5,616,768 A | 4/1997 | Kawata et al. |
| 6,403,820 B1 * | 6/2002 | Hayashi et al. ............ 558/147 |

FOREIGN PATENT DOCUMENTS

| | | |
|---|---|---|
| EP | 0690063 | 1/1996 |
| JP | 63227632 | 9/1988 |
| JP | 5-1079 | 1/1993 |
| JP | 06009661 | 1/1994 |
| JP | 8-67685 | 3/1996 |
| JP | 10168227 | 6/1998 |
| WO | 98/35970 | 8/1998 |

OTHER PUBLICATIONS

English Language Abstract of JP 8–67685.
English Language Abstract of JP 5–1079.
English Language Abstract of JP 63–227632.
English Language Abstract of JP Appln. No. 10–168227.
English Language Abstract of JP Appln. No. 06–009661.

* cited by examiner

Primary Examiner—Robert Gerstl
(74) Attorney, Agent, or Firm—Greenblum & Bernstein, P.L.C.

(57) ABSTRACT

A method of purifying an organic phosphoric ester characterized by treating a crude organic phosphoric ester with an epoxy compound and treating the treated organic phosphoric ester with an alkaline aqueous solution to purify it. The purification method is effective in stably obtaining an organic phosphoric ester reduced in acid value and excellent in heat resistance, hydrolytic resistance, and storage stability, regardless of the kind or amount of the organic phosphoric ester, the treating conditions, etc.

13 Claims, No Drawings

METHOD OF PURIFYING ORGANIC PHOSPHORIC ESTER

TECHNICAL FIELD

The present invention relates to a method of purifying an organic phosphoric ester which is useful as a plasticizer or a flame retardant for a synthetic resin. More particularly, it relates to a purification method for obtaining an organic phosphoric ester which has a low acid value and is excellent in heat resistance, storage stability and hydrolytic resistance.

BACKGROUND ART

Organic phosphoric esters are synthesized by a method for reacting phosphorus oxychloride with an alcohol or phenol under dehydrochlorination, or the like. However, since it is difficult to complete the esterification by this synthesis method, the synthesized organic phosphoric esters show some acid value due to phosphoric acid and chloride derived from the starting materials.

Since the substances that generate the acid value have a bad influence on physical properties such as heat resistance, hydrolytic resistance and storage stability of the organic phosphoric esters, crude organic phosphoric esters are purified to remove the substances generating the acid value, thereby reducing the acid value of the organic phosphoric esters. The purification treatment may be carried out by neutralization using a basic substance, e.g., by wet neutralization using alkali metal hydroxide such as sodium hydroxide or dry neutralization using an alkali earth metal compound such as calcium carbonate and magnesium hydroxide, followed by washing with water, or by distillation.

However, in the case where a highly viscous organic phosphoric ester is subjected to the wet neutralization using alkali metal hydroxide, separation of an aqueous phase and an oily phase is not performed well and takes time. Moreover, there is a problem in that a relatively large amount (e.g., several tens to hundreds of ppm) of alkali metal remains in the separated oily phase. The remaining alkali metal is not preferable because it causes a bad influence on the heat resistance and the hydrolytic resistance of the organic phosphoric ester.

In order to reduce the amount of alkali metal remaining in the organic phosphoric ester, there has been proposed a method of diluting the highly viscous organic phosphoric ester with an organic solvent to reduce the viscosity or a method of salting-out the highly viscous organic phosphoric ester, thereby facilitating the separation of the aqueous phase and the oily phase. However, even in these methods, the alkali metal cannot be eliminated completely and washing with water needs to be carried out many times to get rid of the yet remaining alkali metal. The problem of the remaining alkali metal is also involved in the dry neutralization.

With respect to some organic phosphoric esters, the whole mixture including the crude organic phosphoric ester may be emulsified during the wet neutralization using alkali metal hydroxide, so that the aqueous phase and the oily phase may not be separated well.

In the case of purification by distillation, low molecular weight organic phosphoric esters are purified without suffering from the above-described problem of the remaining alkali metal. However, it is difficult to conduct the purification treatment itself for high molecular weight organic phosphoric esters.

There are other impurities than the alkali metal causing a bad influence on the physical properties such as heat resistance, hydrolytic resistance and storage stability of the organic phosphoric ester. Examples of such impurities include unreacted compounds in which the esterification is not completed, compounds in which phosphoric acid or alcohols and a reaction catalyst are combined and other impurities in a small amount derived from the starting materials.

To eliminate these impurities, only the above-described purification treatment by neutralization or distillation is insufficient and a purification apparatus of high fractionation efficiency is required. However, there is a problem in that the apparatus is expensive and reduces the product yield, thereby increasing the cost.

To solve the problem, there has been developed a purification method of the organic phosphoric ester by treating a crude organic phosphoric ester with an epoxy compound, subjecting the resulting product to thermal treatment in the presence of water, washing the obtained product with water, and then removing residual water (see Japanese Unexamined Patent Publication No. Hei 8(1996)-67685).

According to the method, impurities in the organic phosphoric ester are reacted with the epoxy compound, the reaction product is hydrolyzed in water to convert into a water-soluble compound and the obtained water-soluble compound is removed by washing with water, thereby removing the impurities in the organic phosphoric ester. In this method, it is important to selectively hydrolyze only the compound obtained by the reaction with the epoxy compound. If the hydrolysis is insufficient, the acid value of the organic phosphoric ester cannot be reduced. To the contrary, if the hydrolysis is carried out excessively, the organic phosphoric ester itself to be purified is also hydrolyzed.

Accordingly, in order to purify the organic phosphoric ester efficiently by the above-described method, it is necessary to set the optimum conditions such that the organic phosphoric ester itself is not hydrolyzed during the thermal treatment. The optimum conditions must be established in view of a kind and amount of the organic phosphoric ester, a kind of the epoxy compound, conditions of the thermal treatment (e.g., temperature, time, water amount and the like), as well as an apparatus used, which requires complicated work. Especially, in the case of purifying a large quantity of the organic phosphoric ester in an industry scale, there has been a problem in that the treatment conditions are difficult to establish and thus the acid value of the organic phosphoric ester cannot be reduced sufficiently.

DISCLOSURE OF INVENTION

To solve the above-mentioned problems, the present invention is intended to provide a method of purifying an organic phosphoric ester for stably obtaining the organic phosphoric ester having a low acid value and being excellent in heat resistance, hydrolytic resistance and storage stability, the method being free from the influence by the kind and amount of the organic phosphoric ester as well as the treatment conditions.

According to the present invention, provided is a method of purifying an organic phosphoric ester characterized in that the purification is carried out by treating a crude organic phosphoric ester with an epoxy compound and treating the treated organic phosphoric ester with an alkaline aqueous solution.

BEST MODE FOR CARRYING OUT THE INVENTION

The organic phosphoric esters to be treated by the method of the present invention are compounds that are known in the art and generally used as a plasticizer and/or a flame retardant for a resin. However, they are not particularly limited as long as they contain impurities generated through the synthesis thereof.

The organic phosphoric esters are represented by the general formula (I):

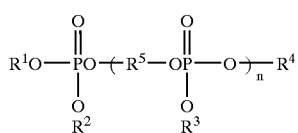

wherein n is an integer of 0 to 30, $R^1$, $R^2$, $R^3$ and $R^4$, the same or different, are an aliphatic hydrocarbon residue or an aromatic hydrocarbon residue when n is 0 or an aromatic hydrocarbon residue when n is 1 to 30, and $R^5$ is a bivalent organic group.

The aliphatic hydrocarbon residue represented by $R^1$, $R^2$, $R^3$ and $R^4$ in the general formula (I) may preferably be a straight-chain or branched-chain alkyl group having a carbon number of 8 to 18. Examples thereof include 2-ethylhexyl, n-octyl, sec-octyl, decyl, dodecyl, hexadecyl, octadecyl and the like.

The aromatic hydrocarbon residue may preferably be an aryl group having a carbon number of 6 to 15. Examples thereof include phenyl, cresyl, xylyl, 2,6-dimethylphenyl, 2,4,6-trimethylphenyl, butylphenyl, nonylphenyl and the like.

The bivalent organic group of $R^5$ may be an alkylene group, an arylene group or the like. Examples thereof include an alkylene group such as methylene, ethylene, trimethylene, propylene, tetramethylene and ethylethylene, an arylene group such as (o-, m- or p-)phenylene, and the following groups:

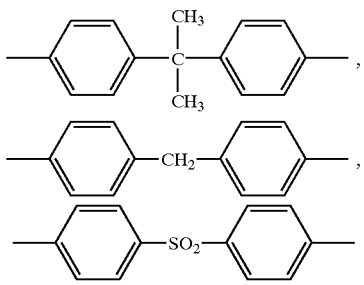

Examples of the organic phosphoric ester compounds of the general formula (I) include not only monomers but also polymers such as dimers and trimers. The organic phosphoric ester to be treated by the method of the present invention may be a simple compound thereof, or a mixture thereof.

The organic phosphoric esters (I) are roughly classified into the organic phosphoric esters having no aromatic hydrocarbon residues and those having aromatic hydrocarbon residues.

Examples of the organic phosphoric esters having no aromatic hydrocarbon residues include trimethyl phosphate, triethyl phosphate, tri-n-propyl phosphate, triisopropyl phosphate, tri(2-ethylhexyl) phosphate, tridecyl phosphate, trioctadecyl phosphate, tris(tribromoneopentyl)phosphate, tris(trichloroneopentyl)phosphate and the like.

Examples of the organic phosphoric esters having aromatic hydrocarbon residues include monomers of organic phosphoric esters such as triphenyl phosphate, [tri(o-, m- or p-)chlorophenyl]phosphate, [tri(o-, m- or p-)bromophenyl] phosphate, [tri(o-, m- or p-)methylphenyl]phosphate, [tri(o-, m- or p-)ethylphenyl]phosphate, [tri(o-, m- or p-)n-propylphenyl]phosphate, [tri(o-, m- or p-)isopropylphenyl] phosphate, [tri(o-, m- or p-)n-butylphenyl]phosphate, [tri(o-, m- or p-)sec-butylphenyl]phosphate, [tri(o-, m- or p-)tert-butylphenyl]phosphate, [tri(o-, m- or p-)octylphenyl] phosphate, [tri(o-, m- or p-)nonylphenyl]phosphate, tris[(2,3-, 2,4-, 2,5-, 2,6-, 3,4- or 3,5-)dimethylphenyl] phosphate, tris[(2,3-, 2,4-, 2,5-, 2,6-, 3,4- or 3,5-) diethylphenyl]phosphate, tris[(2,3-, 2,4-, 2,5-, 2,6-, 3,4- or 3,5-)di-n-propylphenyl]phosphate, tris[(2,3-, 2,4-, 2,5-, 2,6-, 3,4- or 3,5-)diisopropylphenyl]phosphate, tris[(2,3-, 2,4-, 2,5-, 2,6-, 3,4- or 3,5-)di-n-butylphenyl]phosphate, tris[(2, 3-, 2,4-, 2,5-, 2,6-, 3,4- or 3,5-)di-sec-butylphenyl] phosphate, tris[(2,3-, 2,4-, 2,5-, 2,6-, 3,4- or 3,5-)di-tert-butylphenyl]phosphate, tris[(2,3,6-, 2,3,4-, 2,4,6- or 3,4,5-)trimethylphenyl] phosphate, tris[(2,3,6-, 2,3,4-, 2,4,6- or 3,4,5-) triethylphenyl]phosphate, tris[(2,3,6-, 2,3,4-, 2,4,6- or 3,4, 5-)tripropylphenyl]phosphate, cresyldiphenyl phosphate and the like, and condensates thereof such as alkylenebis[di(o-, m- or p-)phenyl phosphate], alkylenebis[di(o-, m- or p-)methylphenyl phosphate], resorcinbis[di(o-, m- or p-)phenyl phosphate], resorcinbis[di(o-, m- or p-)methylphenyl phosphate], resorcinbis[di(o-, m- or p-)ethylphenyl phosphate], resorcinbis[bis(2,3-, 2,4-, 2,5-, 2,6-, 3,4- or 3,5-)dimethylphenyl phosphate], hydroquinonebis[di(o-, m- or p-)phenyl phosphate], hydroquinonebis[di(o-, m- or p-)methylphenyl phosphate], hydroquinonebis[di(o-, m- or p-)ethylphenyl phosphate], hydroquinonebis[bis(2,3-, 2,4-, 2,5-, 2,6-, 3,4- or 3,5-) dimethylphenyl phosphate], bis[di(o-, m- or p-)phenyl phosphate]bisphenol A, bis[di(o-, m- or p-)methylphenyl phosphate]bisphenol A, bis[di(o-, m- or p-)ethylphenyl phosphate]bisphenol A, bis[bis(2,3-, 2,4-, 2,5-, 2,6-, 3,4- or 3,5-)dimethylphenyl phosphate]bisphenol A and the like.

The crude organic phosphoric esters to be treated by the method according to the present invention include impurities generated through the synthesis thereof. Examples of the impurities include alkali metal compounds and Lewis acid compounds that are used as a reaction catalyst, compounds having metal derived from the reaction catalyst (metal in the reaction catalyst) bonded to one of bonds of phosphoric acid, dimers formed by combining phosphoric diesters via metal in the reaction catalyst, compounds formed by combining phosphoric acid as a starting compound and the reaction catalyst, compounds formed by combining alcohols or phenols with the reaction catalyst, unreacted compounds in which esterification is not completed (compounds having P—Cl bond) and the like. In the present invention, these compounds are generally called as "impurities".

The purification method according to the present invention is intended to efficiently remove these impurities. The organic phosphoric esters to be treated are referred to as "crude organic phosphoric esters" to imply that they include the impurities.

The organic phosphoric esters are obtained by a method known in the art. In general, they are obtained by-reacting phosphorus oxychloride with appropriate alcohols or phenols under noncatalystic condition or in the presence of a Lewis acid catalyst (e.g., aluminum chloride, magnesium chloride or titanium tetrachloride).

For example, an aromatic bisphosphate is obtained by reacting phosphorus oxychloride with an aromatic monohydroxy compound (monovalent phenol) in the presence of a Lewis acid catalyst and reacting the obtained diaryl phosphorohalidate with an aromatic dihydroxy compound (bivalent phenol) in the presence of the above-described catalyst (e.g., see Japanese Unexamined Patent Publication No. Hei 5(1993)-1079).

The aromatic bisphosphate is obtained also by reacting phosphorus oxychloride with an aromatic dihydroxy compound, removing unreacted phosphorus oxychloride, and then reacting the resulting product with an aromatic monohydroxy compound (see Japanese Unexamined Patent Publication No. Sho 63(1988)-227632).

Further, the aromatic bisphosphate is obtained also by reacting phosphorus oxychloride with a mixture of an aromatic monohydroxy compound and an aromatic dihydroxy compound.

Examples of phenols used in the above-described manufacture of the organic phosphoric esters include monovalent phenols such as phenol, (o-, m- or p-)methylphenol, (2,3-, 2,4-, 2,5-, 2,6-, 3,4- or 3,5-)dimethylphenol and the like, and bivalent phenols such as resorcin, hydroquinone, bisphenol A, bisphenol F, bisphenol S, biphenol, naphthol and the like.

In the manufacture of the organic phosphoric esters, reaction conditions such as an amount of the reaction catalyst, the ratio between phosphoric acid and alcohols or phenols, the ratio between phosphorus oxychloride and alcohols or phenols, reaction temperature, reaction time and the like are appropriately established.

The thus manufactured organic phosphoric esters generally contain a large amount of impurities. However, according to the purification method of the present invention, the impurities are efficiently removed from the crude organic phosphoric esters.

The purification method according to the present invention is applicable to every one of the organic phosphoric esters of the general formula (I). The purification method of the present invention is also applied suitably to the organic phosphoric esters represented by the following general formula (II), while the acid value thereof is particularly difficult to be reduced by a conventional purification method.

include aromatic solvents such as toluene, xylene and dichlorobenzene, aliphatic solvents such as hexane, heptane and cyclohexane. Where the above-described solvent is used in the synthesis of the organic phosphoric ester, the method of the present invention can be applied without separating the solvent and the organic phosphoric ester. Even if the solvent is separated and left in the organic phosphoric ester, the purification method of the present invention is not hindered.

According to the purification method of the present invention, first, the crude organic phosphoric ester is treated with an epoxy compound (hereinafter referred to as "epoxy treatment"). Through the epoxy treatment, acids in the impurities contained in the crude organic phosphoric ester are masked by epoxy groups.

The epoxy compound may be any one of aliphatic compounds, aromatic compounds, alicyclic compounds and heterocyclic compounds having one or more epoxy group in its structure.

Examples of the aliphatic epoxy compounds include ethylene oxide, propylene oxide, butylene oxide, 3,4-epoxybutanol, polyethylene glycol diglycidyl ether (e.g., having epoxy equivalent of 200 or 400), sorbitol polyglycidyl ether, sorbitan polyglycidyl ether, polyglycerol polyg-

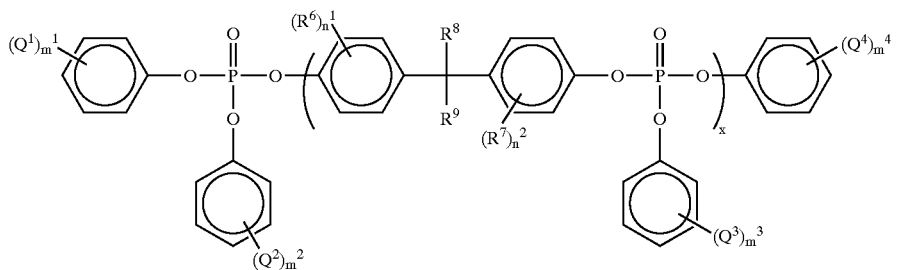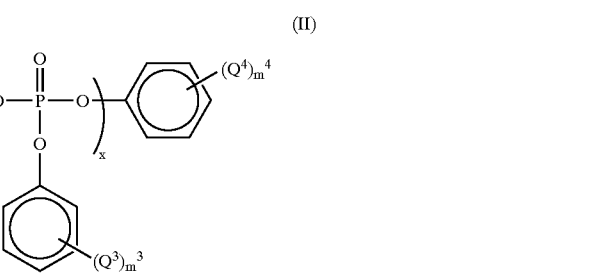

(II)

wherein $Q^1$, $Q^2$, $Q^3$ and $Q^4$, the same or different, are an alkyl group having a carbon number of 1 to 6, $R^6$, $R^7$, $R^8$ and $R^9$ are methyl groups, $m^1$, $m^2$, $m^3$ and $m^4$, the same or different, are an integer of 1 to 3, $n^1$ and $n^2$, the same or different, are an integer of 0 to 2, and x is an integer of 0 to 5.

Examples of the alkyl group having a carbon number of 1 to 6 represented by $Q_1$ to $Q_4$ in the general formula (II) include a straight-chain alkyl group such as methyl, ethyl, n-propyl, n-butyl, n-pentyl and n-hexyl, and a branched-chain alkyl group such as isopropyl, isobutyl, sec-butyl, tert-butyl, isopentyl, tert-pentyl, neo-pentyl and methylpentyl.

Among the organic phosphoric esters of the general formula (II), particular examples to which the present invention is suitably applied are bis(diphenyl phosphate) bisphenol A, bis[di(o-, m- or p-)methylphenyl phosphate]bisphenol A, bis[di(o-, m- or p-)ethylphenyl phosphate]bisphenol A and bis[bis(2,3-, 2,4-, 2,5-, 2,6-, 3,4- or 3,5-)dimethylphenyl phosphate]bisphenol A.

The crude organic phosphoric esters to be treated include solid ones and liquid ones. The purification method of the present invention can be applied to either form. However, the liquid ones are preferable in view of easy handling.

Where a solid organic phosphoric ester or a highly viscous liquid organic phosphoric ester is used, it is preferred to dissolve the solid or liquid organic phosphoric ester in a solvent before applying the method of the present invention thereto.

The solvent used in this case is not particularly limited as long as it is able to dissolve the organic phosphoric ester and does not inhibit the action of an epoxy compound to be inferred in the later description. Specific examples thereof lycidyl ether, pentaerythritol polyglycidyl ether, diglycerol polyglycidyl ether, glycerol polyglycidyl ether, trimethylolpropane polyglycidyl ether, propylene glycol diglycidyl ether, polytetramethylene glycol diglycidyl ether, allyl glycidyl ether, 2-ethylhexyl glycidyl ether, adipic acid diglycidyl ester, dibromoneopentylglycol diglycidyl ether and the like.

Examples of the alicyclic epoxy compounds include 1-methyl-1,4-epoxycycloheptane, 2,3-epoxycyclopentanone, 3,4-epoxycyclooctene, 2,3-epoxynorbornane, 2-(3,4-epoxycyclohexyl)-1,3-dioxolane, 4,5-epoxy-1-p-benzene, 1,2-epoxy-4-p-benzene, 1-(glycidyloxymethyl)-3,4-epoxycyclohexane, 2,3-epoxy-3,5,5-trimethylcyclohexanone, bis(2,3-epoxycyclopentyl) ether and the like.

Examples of the aromatic, heterocyclic and other epoxy compounds include phenyl glycidyl ether, p-tert-butylphenyl glycidyl ether, triglycidyl tris(2-hydroxyethyl) isocyanurate, o-phthalic acid diglycidyl ether, hydroquinone diglycidyl ether, terephthalic acid diglycidyl ether, glycidyl phthalimide, dibromophenyl glycidyl ether, bisphenol A diglycidyl ether, bisphenol S diglycidyl ether and bisphenol F diglycidyl ether, as well as addition reaction products thereof.

Among the above-described epoxy compounds, aliphatic epoxy compounds in a liquid state are preferable in view of their excellent safety and easy availability. Propylene oxide and butylene oxide are particularly preferable.

Reaction conditions of the epoxy treatment are not particularly limited and suitably selected depending on the physical properties and reactivities of the organic phosphoric ester and the epoxy compound. However, it is preferred to dehydrate the crude organic phosphoric ester in advance because the epoxy group reacts with water.

Where ethylene oxide in a gaseous state is used, for example, the treatment may be carried out by blowing ethylene oxide into the crude organic phosphoric ester through an insertion tube.

Where propylene oxide in a liquid state is used, the treatment may be carried out while adding propylene oxide dropwise to the crude organic phosphoric ester or after propylene oxide is added to the crude organic phosphoric ester.

In the case of treating the organic phosphoric esters of the general formula (II) with propylene oxide or butylene oxide, the treatment temperature is preferably about 40 to 160° C., more preferably about 80 to 140° C., in view of their boiling points and reactivities.

The treatment temperature lower than 40° C. is not preferable because the treatment takes a long time. On the other hand, the treatment temperature higher than 160° C. is not preferable because the organic phosphoric ester may be colored or vigorous boiling may occur during the treatment.

The treatment is sufficiently carried out for a treatment time of about 0.5 to 2 hours. For example, the organic phosphoric esters of the general formula (II) are treated in about 0.5 hour with propylene oxide, and about 1 hour with butylene oxide.

In theory, the epoxy compound is used in an amount corresponding to the acid value of the organic phosphoric ester. However, it is preferred to use the epoxy compound in an amount slightly greater than the amount corresponding to the acid value of the organic phosphoric ester in view of reactivity of the epoxy compound and loss by volatilization of a low boiling point epoxy compound, if used.

In general, the ratio between the crude organic phosphoric ester and the epoxy compound is preferably about 1:1 to 1:20 (molar ratio), more preferably about 1:2 to 1:5 (molar ratio) on the basis of the acid value of the crude organic phosphoric ester.

Then, the epoxy-treated organic phosphoric ester is treated with an alkaline aqueous solution (hereinafter this is referred to as an "alkali treatment"). Prior to the alkali treatment, the epoxy-treated organic phosphoric ester is preferably subjected to treatment with water or an acidic aqueous solution (preferably with water). This is called hereinafter an "intermediate treatment". The acidic aqueous solution may be an aqueous solution of hydrogen chloride or phosphoric acid in a concentration of about 0.01 to 1 wt %.

Through the intermediate treatment, acids in the impurities masked with the epoxy compound are hydrolyzed, which improves the efficiency of removing the impurities in the following alkali treatment.

Water or the acidic aqueous solution may be used in an amount of about 0.1 to 5 wt %, preferably about 0.2 to 2 wt % with respect to the crude organic phosphoric ester. The treatment is generally carried out once, but may be repeated as needed.

Specifically, for example, the epoxy-treated organic phosphoric ester is added with water or the acidic aqueous solution, stirred for about 5 minutes to 3 hours, and if necessary, allowed to stand to separate an aqueous phase and an oily phase, and then the aqueous phase is removed.

To the organic phosphoric ester that has gone through the epoxy treatment, which may further be subjected to the intermediate treatment, an alkaline aqueous solution is added. According to the alkali treatment, acids in the impurities masked with the epoxy groups through the epoxy treatment are converted to water-soluble compounds.

The alkaline aqueous solution is not particularly limited as long as it does not inhibit the purification of the organic phosphoric esters. In the present invention, alkali signifies a pH value ranging from about 8 to 13. Examples of the alkaline aqueous solution include, for example, an aqueous solution of alkali metal carbonate such as sodium carbonate and potassium carbonate, alkali metal hydrogencarbonate such as sodium hydrogencarbonate and potassium hydrogencarbonate, alkali metal hydroxide such as sodium hydroxide and potassium hydroxide. Among them, an aqueous solution of alkali metal carbonate is preferable and an aqueous solution of sodium carbonate is particularly preferable.

An alkali compound is used in the alkaline aqueous solution in an amount of 0.1 to 50 molar equivalent, preferably 1 to 5 molar equivalent, with respect to the acid value of the crude organic phosphoric ester before the epoxy treatment.

The alkaline aqueous solution containing the alkali compound in an amount smaller than 0.1 molar equivalent with respect to the acid value of the crude organic phosphoric ester is not preferable because the organic phosphoric ester is not purified sufficiently. Further, the alkaline aqueous solution containing the alkali compound in an amount greater than 50 molar equivalent is not preferable because the removal of the alkali compound will be difficult and emulsification occurs to have influence on the separation.

The concentration of the alkaline aqueous solution is about 0.01 to 10 wt %, preferably about 0.1 to 1 wt %. The alkaline aqueous solution is used in an amount of about 1 to 100 wt %, preferably about 10 to 50 wt %, with respect to the crude organic phosphoric ester, from the calculation based on the above-mentioned amount of the alkali compound.

The treatment temperature is in the range of 60 to 120° C., preferably in the range of 70 to 95° C. At the treatment temperature within the range of 60 to 120° C., alkalis introduced in the treatment system hydrolyze the impurities efficiently without hydrolyzing the organic phosphoric ester.

The treatment time is appropriately determined depending on the treatment temperature. At the treatment temperature in the range of 60 to 120° C., the treatment is carried out sufficiently in about 0.5 to 2 hours. The higher the treatment temperature is, the faster the treatment is completed.

The mixture solution containing the alkali-treated organic phosphoric ester is allowed to stand in order to remove the impurities that have been converted to the water-soluble compounds through the alkali treatment as an aqueous phase. Remaining alkalis are further reduced by washing with water as required. The washing treatment is carried out in the same manner as the above-mentioned intermediate treatment using water performed in advance of the alkali treatment.

Thus, the water-soluble impurities that cause a bad influence on the heat resistance, hydrolytic resistance and storage stability are removed.

Subsequently, water remaining in the organic phosphoric ester is removed, thereby obtaining the purified organic phosphoric ester.

Water may be removed by any one of processes commonly utilized in the art, but evaporation under reduced pressure is preferable. The evaporation under reduced pressure may remove, together with water, a solvent used to dissolve a solid crude organic phosphoric ester and a remaining organic solvent used to synthesize the crude organic phosphoric ester. However, it is preferred that the organic phosphoric ester is dehydrated, dried and subjected to steam distillation to remove such solvents.

Even in the case where the above-mentioned solvents are not used, it is preferred to perform the steam distillation after the removal of water. Accordingly, low boiling point impurities that are hardly soluble to water (e.g., phenol as a synthesis material) are removed.

According to the purification method of the present invention, the organic impurities that are thermally unstable are completely converted to water soluble substances by hydrolysis and then removed. Therefore, excellent purification effect is attained.

According to the purification method of the present invention, the treatment is carried out at relatively low temperature. Therefore, side reactions during the treatment are inhibited and the reduction of the acid value of the organic phosphoric ester is not hindered.

Further, in an industrial view, thermal energy required for heating and time required for heating or cooling can be reduced, so that the organic phosphoric ester having a low acid value is obtained economically and conveniently.

Still according to the purification method of the present invention, the reduction of the acid value of the organic phosphoric ester is not hindered by the amount of the organic phosphoric ester to be treated. Therefore, it is particularly advantageous to the use in an industrial scale.

The "industrial scale" herein signifies that the organic phosphoric ester to be treated is used in an amount generally employed in the industrial scale. Specifically, the amount of the organic phosphoric ester is 500 liter or greater, preferably 1000 liter or greater, more preferably 3000 liter or greater. The upper limit is not particularly established, but may be 30,000 liter or smaller, preferably 20,000 liter or smaller, more preferably 10,000 liter or smaller, due to the restriction by the reaction apparatus.

The organic phosphoric ester obtained by the purification method according to the present invention may be used as a flame retardant for thermoplastic resins such as polyethylene based resins, polypropylene based resins, polybutadiene based resins, polystyrene based resins, polyphenyleneether based resins, polycarbonate based resins, acrylonitrile-butadiene-styrene (ABS) based resins, high impact stylene based resins, acrylonitrile-stylene (SAN) based resins, polyamide based resins, polyester based resins, polyphenylenesulfide based resins and polyacryl based resins, and thermosetting resins such as epoxy based resins, polyurethane based resins, polyimide based resins, phenol based resins, novolac based resins, polyetherimide based resins, melamine based resins and urea resins.

Since the organic phosphoric ester obtained by the method of the present invention has a low acid value, it is not decomposed even at a high treatment temperature during resin molding. Accordingly, a high quality resin mold product having high resistance to heat and discoloration is obtained.

The above-mentioned resin mold product can be obtained by a known method, e.g., by mixing and melt-kneading a flame retardant, a resin and, if necessary, other additives for the resin by using a single-screw extruder, a twin-screw extruder, a Banbury mixer, a kneading mixer, a roller and the like singly or in combination, and molding the obtained resin composition into the form of a plate, a sheet or a film by using a known molding apparatus.

EXAMPLES

The present invention will be described in further detail by way of the following preparation and examples, but they do not limit the scope of the present invention.

Preparation

Phosphorus oxychloride of 10,907 kg and bisphenol A of 3,000 kg were reacted in the presence of magnesium chloride of 30 kg as a catalyst under atmospheric pressure. An excess of phosphorus oxychloride was removed under reduced pressure, and then phenol of 4,932 kg was added and the reaction was maintained under reduced pressure until a theoretical amount of hydrogen chloride was generated. The thus obtained reaction mixture of 9,000 kg was added with toluene of 2,000 kg, and then 7.7% phosphorus acid of 440 kg was added and stirred at 85° C. for 1 hour to remove the catalyst. Further, water of 2,000 kg at about 70° C. was added and allowed to stand to separate an oily phase. The oily phase was dehydrated under reduced pressure to obtain a crude reaction product of 11,000 kg mainly comprised of bis(diphenyl phosphate)bisphenol A as represented by the following formula. The crude reaction product was a transparent, colorless and viscous liquid having an acid value of 1.2 and water content of 150 ppm.

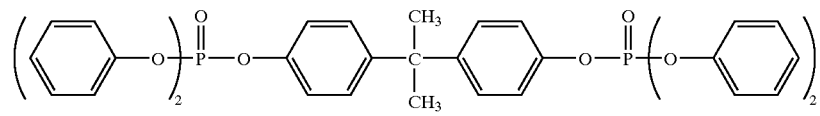

Example

To the crude reaction product of 11.0 t obtained in the above preparation, butylene oxide of 85 kg was added (molar ratio between the crude reaction product and butylene oxide was 1:5 based on the acid value of the crude reaction product) and they were reacted at 120° C. for 2 hours (epoxy treatment).

Then, the reaction mixture was cooled to 85° C., water of 73 kg (0.66 wt % with respect to the crude reaction product) was added thereto and stirred for 2 hours (intermediate treatment).

Further, 0.8 wt % aqueous sodium carbonate solution of 3,000 kg (27.3 wt % with respect to the crude reaction product) was added and stirred at 85° C. for 15 minutes (alkali treatment), and then allowed to stand to separate an oily phase.

The separated oily phase was washed twice with water of 3,100 kg at about 70° C. and subjected to steam distillation at 140° C./50 mmHg for 7 hours to remove impurities such as remaining phenol, thereby obtaining a purified product of about 8.8 t (yield: 97.5% ca.)

The obtained purified product showed the acid value of 0.014 and Na content of 0.7 ppm. Hue based on Hazen's color number method was 25 and purity obtained by gel permeation chromatography (GPC) was 85.4%.

The obtained purified product of 150 g was subjected to a heat resistant test at 250° C. for 3 hours. After the test, the acid value was 0.25, hue based on Gardner's color number method was 1 and purity was 84.9%.

Comparative Example 1

To a crude reaction product of 11.0 t obtained in the same manner as in the above preparation, butylene oxide of 85 kg was added (molar ratio between the crude reaction product and butylene oxide was 1:5 based on the acid value of the crude reaction product) and they were reacted at 120° C. for 2 hours (epoxy treatment).

Then, the reaction mixture was cooled to 85° C., water of 73 kg (0.66 wt % with respect to the crude reaction product) was added and stirred for 2 hours (intermediate treatment).

Subsequently, water of 310 kg at about 85° C. was added and stirred for 1 hour (thermal treatment), and then water of 2,000 kg at about 85° C. was added to separate an oily phase.

The separated oily phase was washed twice with water of 3,100 kg at about 85° C. and subjected to steam distillation at 140° C./50 mmHg for 7 hours to remove impurities such as remaining phenol, thereby obtaining a purified product of about 8.8 t (yield: 97.5% ca.)

The obtained purified product showed the acid value of 0.124 and the Na content of 0.6 ppm.

The results of Example and Comparative Example 1 indicate that the organic phosphoric ester purified by the method of the present invention shows, though it was treated in the industrial scale, a lower acid value and equivalent Na content as compared with those of an organic phosphoric ester purified by a conventional method.

The fact that the acid value is low signifies that impurities derived from phosphoric acid and chloride in the starting materials are reduced. Therefore, the organic phosphoric ester purified by the method of the present invention has physical properties that are close to inherent ones of the organic phosphoric ester and is excellent in heat resistance, hydrolytic resistance and storage stability. Further, since the Na content is small, the organic phosphoric ester purified by the method of the present invention is free from the problem of discoloration.

Comparative Example 2 (Japanese Unexamined Patent Publication No. Hei 8(1996)-67685, Example 1)

To a crude reaction product of 11.0 t obtained in the same manner as in the above preparation, propylene oxide of 68 kg was added (molar ratio between the crude reaction product and propylene oxide was 1:5 based on the acid value of the crude reaction product) and they were reacted at 120° C. for 2 hours (epoxy treatment).

Then, the reaction product was cooled to 85° C. and washed with water of 3,100 kg at 85° C. (intermediate treatment).

Then, it was stirred at 140° C. for 30 minutes (thermal treatment), and allowed to stand to separate an oily phase.

The separated oily phase was washed with water of 3,100 kg at about 85° C., moisture was removed by distillation under reduced pressure, and further subjected to steam distillation at 140° C./50 mmHg for 4 hours to remove impurities such as remaining phenol, thereby obtaining a purified product of about 8.8 t (yield: 97.5% ca.).

The obtained purified product showed the acid value of 0.09 and the Na content of 0.6 ppm. Hue based on Hazen's color number method was 30 and purity obtained by GPC was 85.35%.

The obtained purified product of 150 g was subjected to a heat resistant test at 250° C. for 3 hours. After the test, the acid value was 0.69, hue based on Gardner's color number method was 3 and purity was 82.9%.

The results of Example and Comparative Example 2 are shown in Table 1.

TABLE 1

|  | Example | | Comparative Example 2 | |
| --- | --- | --- | --- | --- |
|  | Before heat resistant test | After heat resistant test | Before heat resistant test | After heat resistant test |
| Acid value | 0.014 | 0.25 | 0.09 | 0.69 |
| Hue | H-25 | G-1 | H-30 | G-3 |
| Purity | 85.4% | 84.9% | 85.35% | 82.9% |

H and G stand for the hues based on Hazen's color number method and Gardner's color number method, respectively.

Table 1 indicates that the organic phosphoric ester purified by the method of the present invention shows higher heat resistance than that of an organic phosphoric ester purified by a conventional method, even if it was treated in the industrial scale.

The purification method according to the present invention does not require any operations for establishing complicated conditions that have been conducted in the conventional method. Further, by a simple treatment using an alkaline aqueous solution, the impurities that cause a bad influence on the physical properties such as heat resistance, hydrolytic resistance and storage stability can be removed. Moreover, even if the alkali metal compound, which may cause discoloration of the organic phosphoric ester, is used during the treatment, it is hardly left after the treatment and thus the problem of the discoloration is eliminated.

Further, according to the purification method of the present invention, the organic phosphoric ester even in an amount in the industrial scale can be treated.

The organic phosphoric ester purified by the method of the present invention has a low acid value and is excellent in heat resistance, hydrolytic resistance and storage stability. Therefore, even if it is added to a resin as a plasticizer or a flame retardant, it maintains stability at a molding temperature of the resin and thus does not cause any change in composition.

What is claimed is:

1. A method of purifying an organic phosphoric ester, comprising treating a crude organic phosphoric ester with an epoxy compound and thereafter treating it with an alkaline aqueous solution.

2. A method according to claim 1, wherein the epoxy compound is propylene oxide or butylene oxide.

3. A method according to claim 1, wherein the ratio between the crude organic phosphoric ester and the epoxy compound is 1:1 to 1:20 (molar ratio) based on an acid value of the crude organic phosphoric ester.

4. A method according to claim 1, wherein the treatment with the epoxy compound is carried out at 40 to 160° C.

5. A method according to claim 1, wherein the method further comprises treating the organic phosphoric ester with water or an acidic aqueous solution after the treatment with the epoxy compound and in advance of the treatment with the alkaline aqueous solution.

6. A method according to claim 1, wherein the alkaline aqueous solution is an aqueous solution of an alkali metal carbonate.

7. A method according to claim 6, wherein the aqueous solution of alkali metal carbonate is an aqueous solution of sodium carbonate.

8. A method according to claim 1, wherein an amount of an alkali compound in the alkaline aqueous solution is 0.1 to 50 molar equivalent with respect to the acid value of the crude organic phosphoric ester which is not yet treated with the epoxy compound.

9. A method according to claim 1, wherein a concentration of the alkaline aqueous solution is 0.01 to 10 wt %.

10. A method according to claim 1, wherein the treatment with the alkaline aqueous solution is carried out at 60 to 120° C.

11. A method according to claim 1, wherein the organic phosphoric ester is a compound represented by the general formula (II):

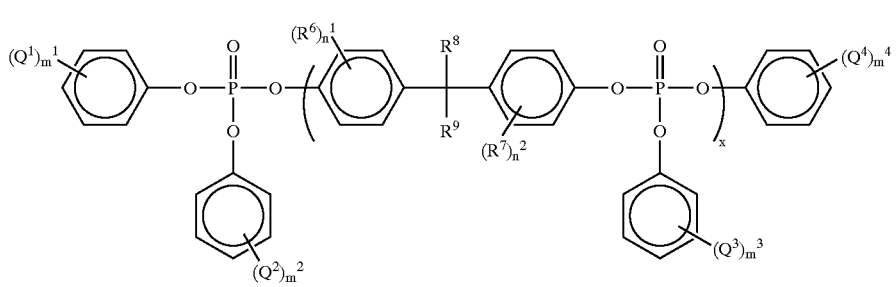

(II)

wherein $Q^1$, $Q^2$, $Q^3$ and $Q^4$, the same or different are an alkyl group having a carbon number of 1 to 6, $R^6$, $R^7$, $R^8$ and $R^9$ are methyl groups, $m^1$, $m^2$, $m^3$ and $m^4$, the same or different, are an integer of 1 to 3, $n^1$ and $n^2$, the same or different, are an integer of 0 to 2, and x is an integer of 0 to 5.

12. A method according to claim 1, wherein the crude organic phosphoric ester is dehydrated in advance of the treatment with the epoxy compound.

13. A method acceding to claim 1, wherein the organic phosphoric ester that has been treated with the alkaline aqueous solution is washed with water and subjected to steam distillation.

* * * * *